US012207945B2

(12) United States Patent
Sheldon et al.

(10) Patent No.: US 12,207,945 B2
(45) Date of Patent: Jan. 28, 2025

(54) WEARABLE CARDIOVASCULAR MONITORING DEVICE

(71) Applicant: 42 Health Sensor Holdings LTD, Calgary (CA)

(72) Inventors: Robert Stanley Sheldon, Calgary (CA); Daniel Edward Roach, Calgary (CA)

(73) Assignee: 42 Health Sensor Holdings LTD, Calgary (CA)

(*) Notice: Subject to any disclaimer, the term of this patent is extended or adjusted under 35 U.S.C. 154(b) by 590 days.

(21) Appl. No.: 16/850,317

(22) Filed: Apr. 16, 2020

(65) Prior Publication Data

US 2020/0330038 A1 Oct. 22, 2020

Related U.S. Application Data

(60) Provisional application No. 62/836,317, filed on Apr. 19, 2019.

(51) Int. Cl.
 *A61B 5/00* (2006.01)
 *A61B 5/022* (2006.01)
 *A61B 5/024* (2006.01)

(52) U.S. Cl.
CPC ........ *A61B 5/6838* (2013.01); *A61B 5/02225* (2013.01); *A61B 5/02241* (2013.01); *A61B 5/6815* (2013.01); *A61B 5/02438* (2013.01); *A61B 2560/0223* (2013.01)

(58) Field of Classification Search
CPC ... A61B 5/6838; A61B 5/6815; A61B 5/6816; A61B 5/02225; A61B 5/0022; A61B 5/02241; A61B 2560/0223; A61B 5/02438

USPC .......................................... 600/499
See application file for complete search history.

(56) References Cited

U.S. PATENT DOCUMENTS

| 3,412,729 | A | 11/1968 | Smith |
| 7,641,614 | B2 | 1/2010 | Haruhiko et al. |
| 8,588,880 | B2* | 11/2013 | Abdul-Hafiz ........ A61B 5/1455 600/344 |
| 2005/0148885 | A1* | 7/2005 | Tweed .................. A61B 5/411 600/490 |

(Continued)

FOREIGN PATENT DOCUMENTS

| CN | 105982659 A | * | 10/2016 |
| JP | 2006280791 A | | 10/2006 |

(Continued)

OTHER PUBLICATIONS

International Search Report and Written Opinion, dated Aug. 3, 2020, received in connection with corresponding International Patent Application No. PCT/IB2020/053623.

(Continued)

*Primary Examiner* — Jacqueline Cheng
*Assistant Examiner* — Jonathan E. Cooper
(74) *Attorney, Agent, or Firm* — Meunier Carlin & Curfman LLC

(57) ABSTRACT

A wearable cardiovascular monitoring device comprises a force sensor configured for a blood pressure measurement using an ear of a human. The device is worn over the ear, with a first vise face of an ear-vise contacting one side of the ear, and a second vise face of the ear-vise contacting another side of the ear. Force is applied to ear through one or both of the vise faces and is used to measure blood pressure.

11 Claims, 11 Drawing Sheets

(56) References Cited

U.S. PATENT DOCUMENTS

| | | | |
|---|---|---|---|
| 2007/0135717 A1 | 6/2007 | Uenishi et al. | |
| 2008/0091112 A1* | 4/2008 | Kondo | A61B 5/02241 600/485 |
| 2008/0097228 A1 | 4/2008 | Aihara et al. | |
| 2008/0243008 A1* | 10/2008 | Habu | A61B 5/6815 600/494 |
| 2009/0112071 A1* | 4/2009 | LeBoeuf | A61B 5/0261 600/301 |
| 2009/0264774 A1 | 10/2009 | Kondo et al. | |
| 2010/0217100 A1* | 8/2010 | LeBoeuf | A61B 5/6826 600/382 |
| 2010/0234743 A1* | 9/2010 | Kohyama | A61B 5/02233 600/499 |
| 2010/0331631 A1* | 12/2010 | MacLaughlin | A61B 5/7445 600/324 |
| 2015/0080751 A1* | 3/2015 | Regh | A61B 5/02225 600/494 |
| 2015/0126825 A1 | 5/2015 | Leboeuf et al. | |
| 2015/0309535 A1* | 10/2015 | Connor | A61B 5/1477 361/679.03 |
| 2018/0055387 A1* | 3/2018 | Takahashi | A61B 5/02108 |
| 2018/0333244 A1* | 11/2018 | Hanks | A61B 5/7278 |
| 2019/0059825 A1* | 2/2019 | Baruch | A61B 5/02225 |
| 2019/0076032 A1* | 3/2019 | Park | A61B 5/6885 |

FOREIGN PATENT DOCUMENTS

| | | | | |
|---|---|---|---|---|
| JP | 2007259957 A | | 10/2007 | |
| JP | 2008043515 A | | 2/2008 | |
| KR | 20180024525 A | | 3/2018 | |
| WO | 2006038628 A1 | | 4/2006 | |
| WO | WO-2007043349 A1 | * | 4/2007 | A61B 5/02241 |
| WO | WO-2009032074 A1 | * | 3/2009 | A61B 5/14552 |
| WO | WO-2010108287 A1 | * | 9/2010 | A61B 5/002 |

OTHER PUBLICATIONS

Extended European Search Report, dated Nov. 21, 2022, received in connection with corresponding EP Patent Application No. 20791316.1.

* cited by examiner

WEARABLE CARDIOVASCULAR MONITORING DEVICE

CROSS-REFERENCE TO RELATED APPLICATIONS

This application claims the benefit of priority to U.S. Provisional Patent Application No. 62/836,317, filed on Apr. 19, 2019, entitled "Systems and Methods for Non-Invasive Detection of Blood Pressure," the contents of which are hereby incorporated by reference in its entirety.

BACKGROUND

In order to diagnose or monitor a patient experiencing syncope or hypertension, a physician requires patient blood pressure (BP) data. A measurement taken by the physician during an in-clinic appointment captures only the patient's blood pressure at the time of the reading and does not detect transient changes in blood pressure throughout a typical day. Often the one-time reading is insufficient, and thus BP data collected over an extended period is ordered by the physician. Typically, this data is collected using an ambulatory blood pressure (BP) monitor over a period of 24 hours.

A standard ambulatory BP monitor consists of an automatically inflatable cuff worn on the user's arm for the diagnostic period, connected by an air supply tube to a monitoring device. These monitors are cumbersome to wear and interfere with normal activity as they automatically inflate and squeeze the user's arm to measure blood pressure approximately every 15 to 30 minutes of the day. It is recommended that the user limit movement and sit down, if possible, when the cuff is inflating and taking a reading. Disadvantageously, a user may not experience a typical day when interrupted regularly with an inflating cuff. Additionally, with measurements taken at a specified time interval, the data collected is a series of individual measurements, rather than a continuous, uninterrupted stream of data, thereby not truly providing full blood pressure data over the monitoring period for the patient.

Other devices have been proposed to measure blood pressure without an inflatable cuff. U.S. Patent Application Publication No. 2007/0135717 to Uenishi et al. includes a pressure detection mechanism, however it does not allow for continuous measurement, but rather provides a single measurement similar to a blood pressure cuff.

SUMMARY

In an implementation, a wearable cardiovascular monitoring device comprises: a first portion configured to be worn on a first side of an ear of a human with a first vise face for contacting the first side of the ear; a second portion configured to be worn on a second side of the ear with a second vise face for contacting the second side of the ear, wherein the second portion comprises a force sensor configured for a blood pressure measurement; and a third portion configured to be worn over the ear and attached to the first portion and the second portion.

In an implementation, a cardiovascular monitoring device comprises: an ear-vise comprising a first vise face and a second vise face configured to apply pressure to an ear; and a sensor for measuring blood pressure using the pressure applied to the ear.

In an implementation, a method for blood pressure measurement of a person comprises: setting a vise acquisition force of a wearable cardiovascular monitoring device on an ear of the person; monitoring a vise force of the wearable cardiovascular monitoring device on the ear; acquiring data from the wearable cardiovascular monitoring device on the ear; and outputting the acquired data.

This summary is provided to introduce a selection of concepts in a simplified form that are further described below in the detailed description. This summary is not intended to identify key features or essential features of the claimed subject matter, nor is it intended to be used to limit the scope of the claimed subject matter.

BRIEF DESCRIPTION OF THE DRAWINGS

The foregoing summary, as well as the following detailed description of illustrative embodiments, is better understood when read in conjunction with the appended drawings. For the purpose of illustrating the embodiments, there is shown in the drawings example constructions of the embodiments; however, the embodiments are not limited to the specific methods and instrumentalities disclosed. In the drawings.

DETAILED DESCRIPTION

Compared to the fingertip, wrist and upper arm, the ear is a very stable place to detect arterial blood pressure (BP). Ears do not swing around when a person walks or exercises, ears do not experience signal artifact due to muscle activation/deactivation, and the arch of cartilaginous connection to the head provides an out-of-the-way stable attachment structure. Moreover, most ears manifest a planar cartilage element located somewhere in the vicinity of pulsating arteries. The planar cartilage element need not be large, only large enough to accommodate the planar compression of the arteries across the ear tissue. Curved cartilage presents a greater challenge, since any trans ear tissue compression in the presence of curved cartilage will result in differential compression as the planar face of the compression device attempts to uniformly compress the curved cartilage.

Figure 1:
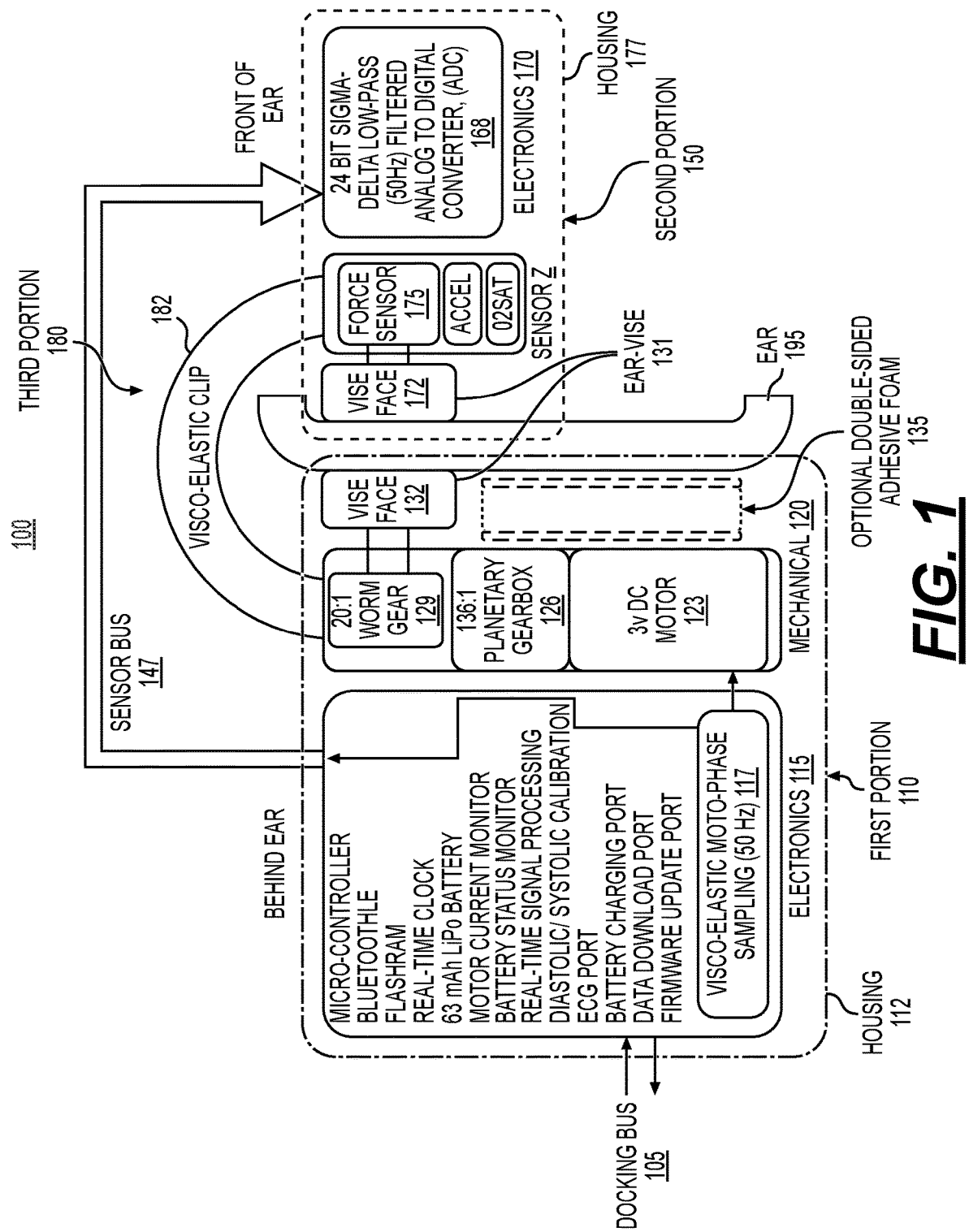
FIG. 1 is a diagram of an implementation of a wearable cardiovascular monitoring device.

FIG. 1 is a diagram of an implementation of a wearable cardiovascular monitoring device 100. The device 100 comprises a first portion 110 and a second portion 150 that are affixed to each other by a third portion 180. The device 100 may be worn over an ear 195, for example. In some implementations, the first portion 110 may be worn behind the ear 195 and the second portion 150 may be worn in front of the ear 195. The third portion 180 may be attached to the first portion 110 and the second portion 150 to join the first portion 110 and the second portion 150, and may be worn over the ear 195, in some implementations.

The first portion 110 comprises an electronics portion 115 and a mechanical portion 120. The first portion 110 may be comprised within a housing 112. In some implementations, the electronics portion 115 may comprise one or more aspects, features, or components of a computing device, such as the computing device 1100 described with respect to FIG. 11. In some implementations, the electronics portion 115 may comprise one or more of a micro-controller, BluetoothLE (Bluetooth Low Energy, also referred to herein at BT), flash RAM and/or other storage or memory, a real-time clock, a battery such as a 63 mAh LiPo battery, a motor current monitor, a battery status monitor, real-time signal processing, diastolic/systolic calibrations, an ECG port, a battery charging port, a data download port, and/or a firmware update port. The electronics portion 115 may be configured to perform visco-elastic moto-phase sampling 117 (50 Hz). In some implementations, the battery charging port and/or the data download port are configured to attach to, and communicate via, a docking bus 105.

In some implementations, the mechanical portion 120 comprises a motor 123 such as a 3v DC motor, a gearbox 126 such as a 136:1 planetary gearbox, and a gear 129 such as a 20:1 worm gear. A vise face 132 is also comprised within the first portion 110. In some implementations, the vise face 132 is affixed to the gear 129. When the device 100 is worn, the vise face 132 is disposed in contact with the ear 195. Optionally, a piece of foam 135, such as double-sided adhesive foam, is disposed in the first portion 110 and may rest against the ear 195 or the housing 112 when the device 100 is worn.

The second portion 150 comprises a sensor 160 and an electronics portion 170. The sensor 160 comprises O2Sat, accel, and a force sensor 175. A vise face 172 is also comprised within the first portion 150. In some implementations, the vise face 172 is affixed to the force sensor 175. When the device 100 is worn, the vise face 172 is disposed in contact with the ear 195. The second portion 150 may be comprised within a housing 177.

Figure 11:
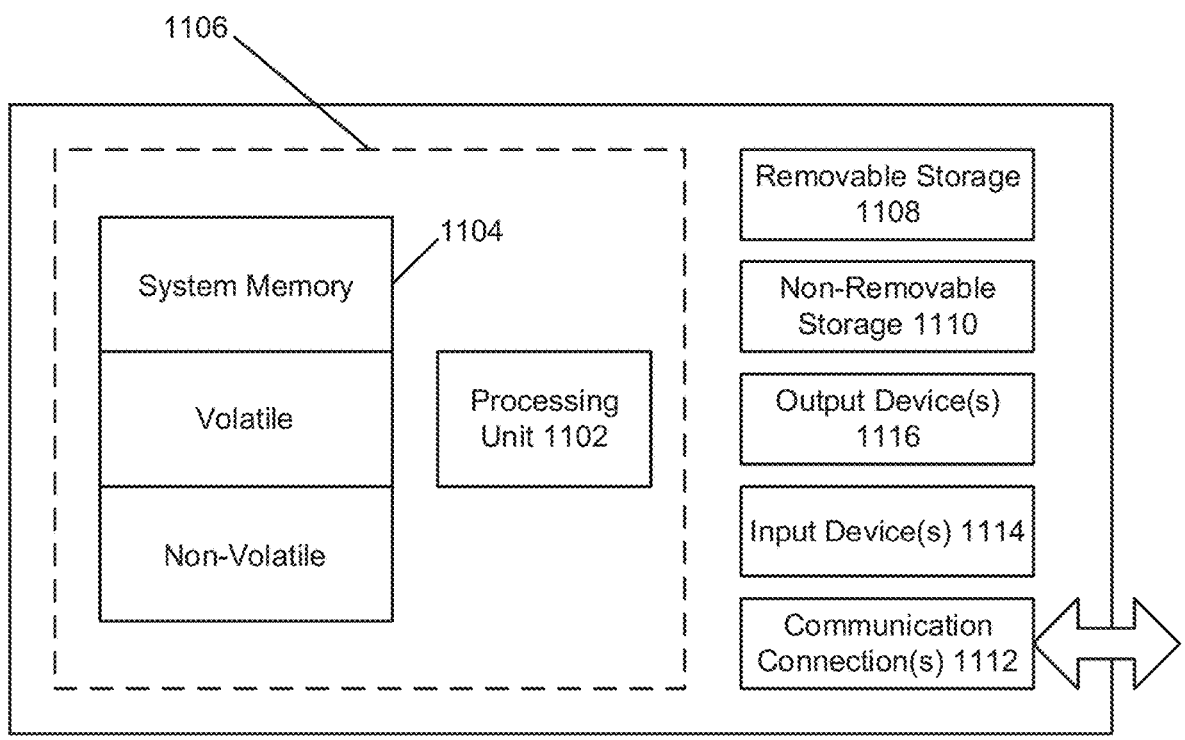
FIG. 11 shows an exemplary computing environment in which example embodiments and aspects may be implemented.

Like the electronics portion 115, the electronics portion 170 may comprise one or more aspects, features, or components of a computing device, such as the computing device 1100 described with respect to FIG. 11. The electronics portion 115 and the electronics portion 170 may be in communication with each other via a sensor bus 147. The electronics portion 115 and the electronics portion 170 may be comprised within the same computing device or may be disposed in separate computing devices, depending on the implementation.

The electronics portion 115 and/or the electronics portion 170 may include a control system and/or a processor. The processor may comprise a processing circuit and memory that stores machine instructions that, when executed by the processing circuit, cause the processing circuit to perform one or more of the operations and methods described herein. The processing circuit may optionally contain a cache memory unit for temporary storage of instructions, data, or computer addresses. The control system further includes a data storage of any conventional type operable to store a date generated or received by the device 100. It will be appreciated that the processing circuit may contain instructions to convert measurements to blood pressure data. The control system may also include an input/output interface such as a radio transmitter, ethernet adapter, USB connection or the like for providing communication between the processing circuit and external systems.

The device 100 may be considered to include an ear-vise 131 which comprises vise face 132 and vise face 172. For every heartbeat, the pulsating arteries inflate and deflate with oxygen-rich blood. It is estimated that the arterial beds within the ear may increase in thickness by as much as 50-100 microns per beat. An ear-vise 131 is an oscillometric device such that a confining pressure is applied to some tissue and the contained pulsating arteries inflate and deflate under confining pressure causing some pulsatile changes in a measured parameter of the tissue. In the more familiar tissue geometries such as the finger or upper arm, the confining pressure is applied radially around a cylindrical bone. The pressurized cuff produces a radial confining pressure that serves to flatten the tissue and arteries against the circumscribed cylindrical bone element. At the ear, the device 100 applies the confining pressure perpendicular to the planar surface via the ear-vise 131.

In some implementations, the housing such as the housing 112 and the housing 177 may be comprised of a polymer, such as Somos® 9120 polymer, and may be fabricated using stereolithography (SLA). However, this material and fabrication technique is not intended to be limiting as any appropriate material(s) may be used for the housing(s) and any appropriate fabrication technique(s) may be used to fabricate the housing(s).

The third portion 180 may comprise a visco-elastic clip 182 that connects the mechanical portion 120 of the first portion 110 with the sensor portion 160 of the second portion 150. Although the clip is described as visco-elastic, it is not limited thereto, and may be made of a metal or ceramic or other material(s) depending on the implementation. Similarly, the housing, gearbox, and other components may be made of various materials depending on the implementation.

The visco-elastic moto-phase sampling 117 of the first portion 110 samples the motor 123 and provides the samples via the sensor bus 147 to the electronics portion 170 of the second portion 150 (e.g., to the analog to digital converter (ADC) 168 of the electronics portion 170).

Figure 2:
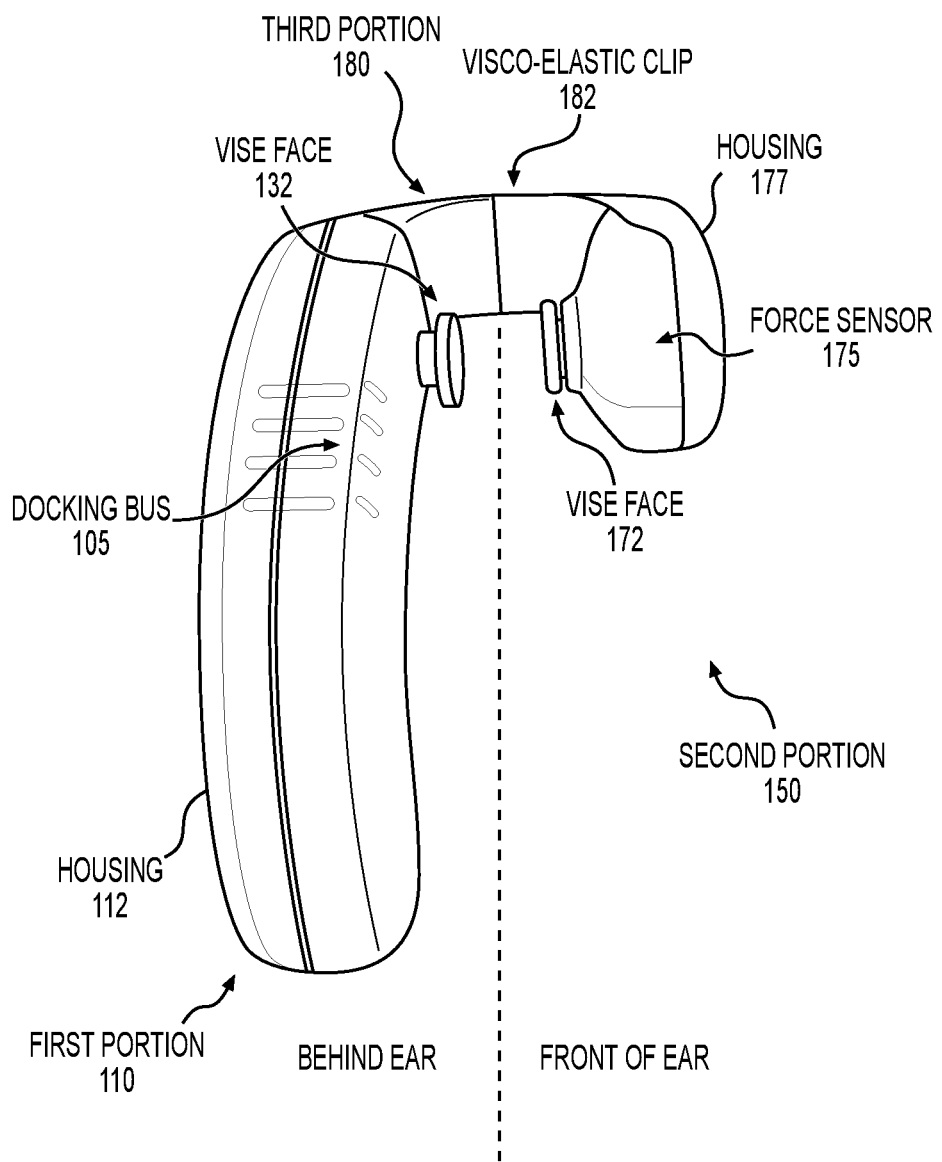
FIG. 2 is another illustration of the wearable cardiovascular monitoring device.

FIG. 2 is another illustration 200 of the wearable cardiovascular monitoring device 100. The illustration 200 shows the first portion 110, the second portion 150, and the third portion 180, along with the docking bus 105, the vise face 132, the vise face 172, and the force sensor 175. The visco-elastic clip 182 is also shown, along with the housing 112 and the housing 177.

A sensing technique monitors the pulsatility of some measured parameter as the confining pressure is varied. In most instances, the compression drive is programmed to cause a steady increase in tissue confining compression until the pulsatility of the measured parameter is statistically eliminated (i.e., BP occlusion), and then a little more. At this point, the confining pressure exceeds the arterial systolic BP by 20-50 mmHg; upon the slow controlled decrease in confining pressure, the systolic BP eventually exceeds the decreasing confining pressure and the pulsatility becomes detectable again. This point is used in determining the systolic BP. As the confining pressure further decreases, the magnitude of the pulsatility (or oscillations) increases eventually reaching a maximum, peak to trough magnitude. Empirically, this unique point is used to establish the diastolic BP. As the confining pressure further decreases, the pulsatility magnitude slowly decreases until the confining pressure reaches zero. At this point, the diastolic and systolic pressures are determined. For continuous blood pressure measurements, some comfortable confining pressure is applied to the tissue and a continuous pulsatile trace is obtained. Thus, immediately one can correlate the just determined systole and diastole to the diastolic point and systolic points on the continuous trace. For as long as the trace pulsatile signal stays well-behaved, and does not deviate too drastically in shape or magnitude, then it is possible to estimate the continuous BP. When large signal aberrations occur in the pulsatile signal (typically at times of posture changes, large skeletal muscle activation, and respiratory changes), these deviations are detected via signal processing and a new calibration is automatically started, or a request for a new calibration is generated to the user.

There are many potential pulsatile signals and techniques that respond in a manner for use in oscillometric BP determination. If the ear-vise is sufficiently flexible (e.g., allowing for approximately 100 micron pulsatile displacement under normal BP conditions), then this micron displacement can be measured in several ways. These displacement techniques all rely on the ability to convert micro displacement to force through some sort of known stress/strain relationship. Typically, some element of the ear-vise assembly, such as one of the vise faces, is disposed or mounted such that the compressive force from the gearbox motor and from pulsatile BP changes cause micron scale displacements that are then converted to a voltage proportional to force. In some embodiments, the displacement is measured across the compressed ear tissue. In other embodiments, the measured displacements can be on one side of the ear (e.g., behind an ear-vise face).

In an implementation, a Hall Effect Transducer (HET) may be disposed on one side of the ear tissue and coaxially coupled to the magnet dipole of a disk magnet on the other side of the ear tissue. As the distance between the disk magnet and the HET changes via the gearbox motor and the changing BP, the HET produces a change in voltage proportional to the change in detected magnetic field strength. This is a straightforward technique to implement, and requires no sophisticated radio-frequency (RF) electronics for signal detection, thus it is relatively low power. The Hall Effect Transducer route is feasible, but it has a larger footprint, consumes more current when active (e.g., 2 mA), and requires a manufacturing step for calibration.

In an implementation, as the BP varies in a pulsatile manner, it is capable of expanding arteries and ear tissue beds. Collectively, within the arterial bed under consideration, the expansion and contraction of arteries can exert an average force change on the ear-vise faces. This changing force can be converted into a voltage signal that can be sampled in many ways, including a MEMS force gauge. A micro-electrical mechanical systems (MEMS) force gauge is a much less expensive and smaller version of the Wheatstone bridge force gauge. These are smaller and much less expensive and they exhibit similar thermal stability. Because they are an order of magnitude smaller than a traditional strain gauge, these MEMS force gauges exhibit reduced self-deformation characteristics, and reduced switching/settling times.

Real-time, miniaturized hardware and signal processing are making tremendous strides with the advent of specialized processing modules. Thus, there will be a growing use of sophisticated signal processing. In some implementations, ear-mounted BP units will have no macro moving parts at all, and the signal is derived from tiny sensors and sophisticated real-time signal processing. Alternatively, other ear-mounted platforms offer a quick macro-mechanical solution for measuring continuous blood pressure. In some implementations, a micro-processor controlled motor/gearbox/worm gear linear-actuator assembly is used to control the mechanical aspect of the ear tissue under investigation. As listed above, there are many sensors which can be used to detect the BP pulsatility under varying confining pressures. Another consideration for ear-based BP measurement is power consumption. In some implementations, the gearbox motor is only used during calibration, and thus is not a long-term drain on the battery. It is also important for the sensor package not to consume too much power. The sensors with the least current drain are the MEMS force sensor and the larger sized Wheatstone bridge strain gauges. These are passive resistive sensors; they have rapid turn-on times and can thus be turned off during intervals between samples, and these devices draw micro-amps. These force sensors are immune to changing ambient light conditions that can severely affect optical sensors. These force sensors inherently adjust for changing temperatures. The MEMS force sensor also has the smallest footprint and is pre-calibrated.

Furthermore, the device may be combined with one or more other sensors for use in monitoring the status of a patient including, breathing rate, oxygen saturation, activity level, temperature and whether the patient is awake or sleeping. Examples of such additional sensors may include without limitation, oximeters, tricolor LED/phototransistors, accelerometers, microphones, nasal thermistors, thermometers, skin galvanometers, linear photo transistor arrays, ultrasonic probes and arrays, infra-red LED/phototransistor pairs, RF impedance plethysmography and piezoelectric vibration elements.

Advantageously, when the apparatus as set out above is applied to the ear, it is known that the ear does not include any muscle therein. Additionally, the ear is not located at an extremity of the body which is significantly subjected to movement as is a hand or foot. Therefore, the measurements obtained from such location will not be dependent upon the movement and activity of the user.

Figure 3:
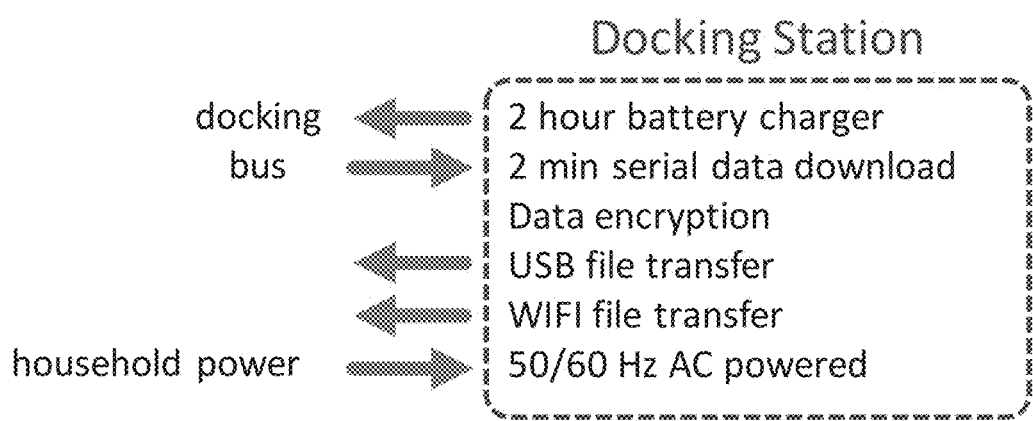
FIG. 3 is a diagram of an implementation of a docking station that can be used with a wearable cardiovascular monitoring device.

FIG. 3 is a diagram of an implementation of a docking station 300 that can be used with a wearable cardiovascular monitoring device such as the device 100 or the device 200. The docking station 300 may comprise one or more components configured to perform one or more of battery charging (e.g., a 2 hour battery charger), serial data download (e.g., a 2 min serial data download), data encryption, file transfer (e.g., USB file transfer, WiFi file transfer, etc.), and 50/60 Hz AC powered. The docking station 300 may be configured to receive a docking bus from a wearable cardiovascular monitoring device, such as the docking bus 105 from device 100 or a docking bus from the device 200.

Figure 4:
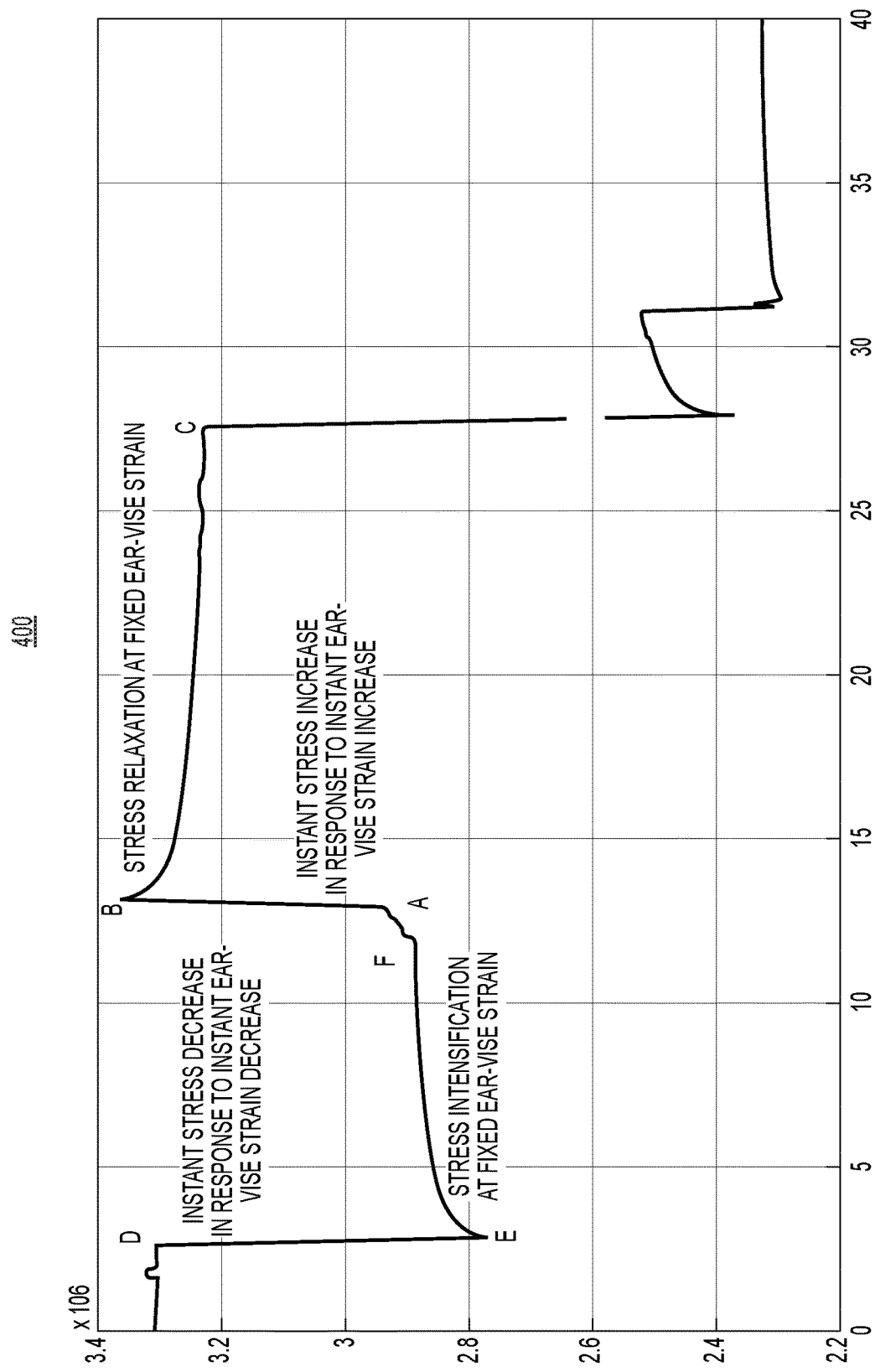
FIG. 4 is a chart that shows example visco-elastic responses to instant changes in ear-vise strain.

FIG. 4 is a chart 400 that shows example visco-elastic responses to instant changes in ear-vise strain using a device, such as the device 100 of FIG. 1. Although FIG. 4 is described with respect to the device 100 of FIG. 1, this is not intended to be limiting, as the techniques described with respect to FIG. 4 may be used with any wearable cardiovascular monitoring device contemplated herein. More particularly, compression/decompression tests performed by the ear-vise on an incompressible steel disk displayed visco-elastic response behavior as seen in FIG. 4.

In FIG. 4, at point A, the DC motor 123 is switched on briefly causing the ear-vise (comprising vise faces 132, 172) to rapidly increase the stress across the steel disk until such time that the motor 123 is switched off at point B.

At point B, the measured stress begins to immediately decay, while the motor 123 is switched off. The high gear ratio of the planetary gearbox 126 (136:1) and the worm gear 129 (20:1) ensure that the ear-vise position remains locked when the power to the motor is 123 removed. Thus, the observed stress decay kinetic is due to the visco-elastic response behavior of the Somos 9120 polymer. The visco-elastic clip 182 is the most readably deformable piece of polymer subject to the compression forces of the ear-vise; thus, FIG. 4 represents the visco-elastic response behavior of the visco-elastic clip 182. Note that the compression forces exponentially decay towards an asymptotic value at point C. This stress relaxation is a common response of polymers to rapidly applied strain.

At point D, the DC motor 123 is switched on, in reverse, briefly causing the ear-vise to rapidly decrease the strain on the visco-elastic clip 182. At point E, the motor 123 is switched off, the ear-vise position is locked, and there is a spontaneous intensification of the measured stress; it increases asymptotically towards point F. Note that the kinetic of stress intensification (although opposite in sign) closely matches the kinetic of the stress relaxation. In this instance, this intensification is attributed to polymer memory, where the polymer is slowly trying to revert to its former shape, thus increasing the stress. By numerically comparing the decay kinetics of stress relaxation vs. the kinetics of stress intensification, it was found that both kinetics were best fit by a bi-exponential decay process. Moreover, the decay coefficients of both were the same.

Figure 5:
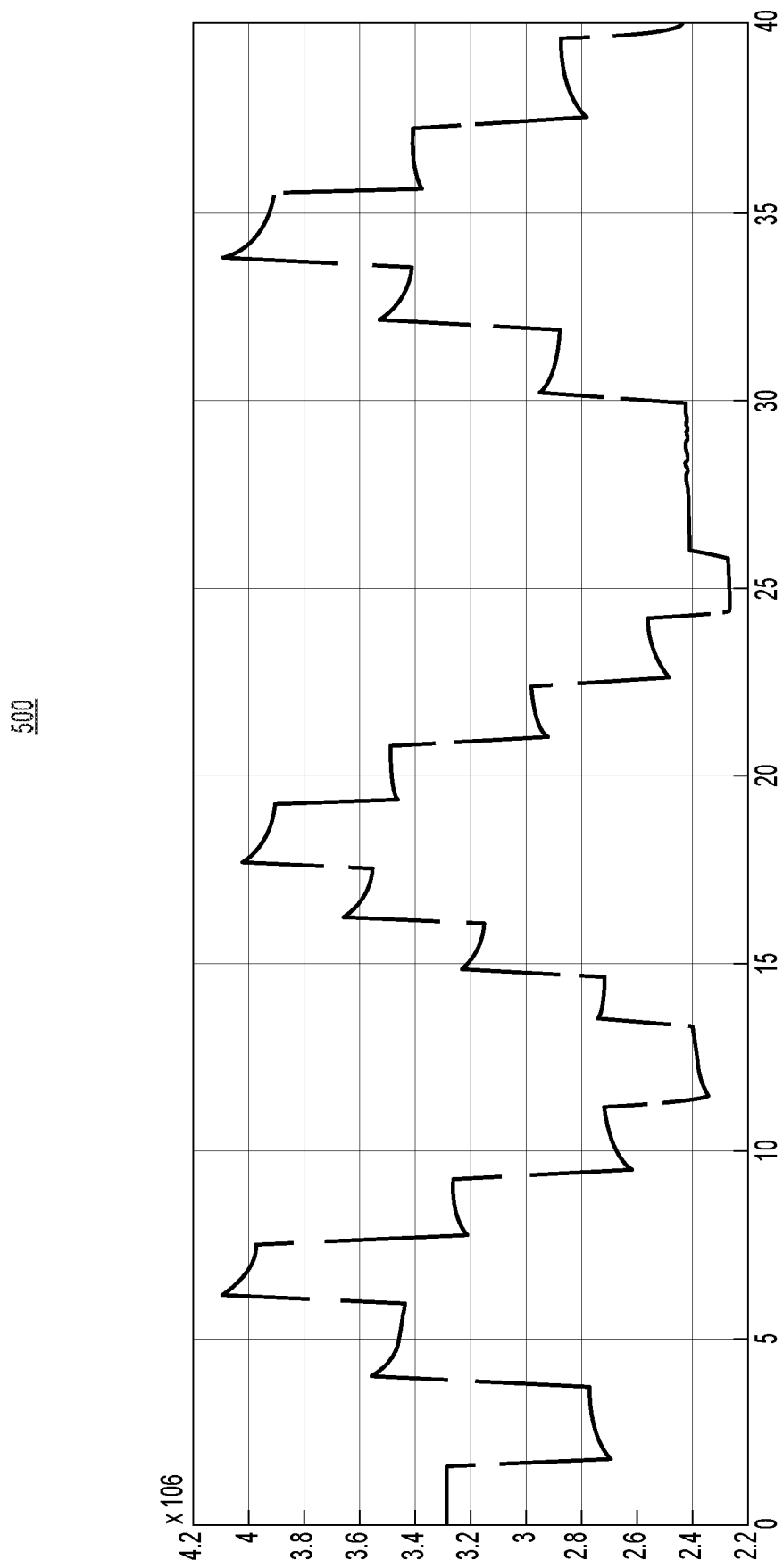
FIG. 5 is a chart that shows an example of three cycles of ear-vise stop-and-go compression and decompression on an incompressible steel disk.

FIG. 5 is a chart 500 that shows an example of three cycles of ear-vise stop-and-go compression and decompression on an incompressible steel disk. In other words, FIG. 5 shows three cycles of stop-and-go stress increase followed by stop-and-go stress decrease, as the ear-vise attempts to strain the incompressible steel disk. Note that the visco-elastic kinetics always manifest when the motor is stopped. Immediately after rapid compression, the spontaneous visco-elastic response is relaxation; after rapid decompression the spontaneous visco-elastic response is intensification.

Figure 6:
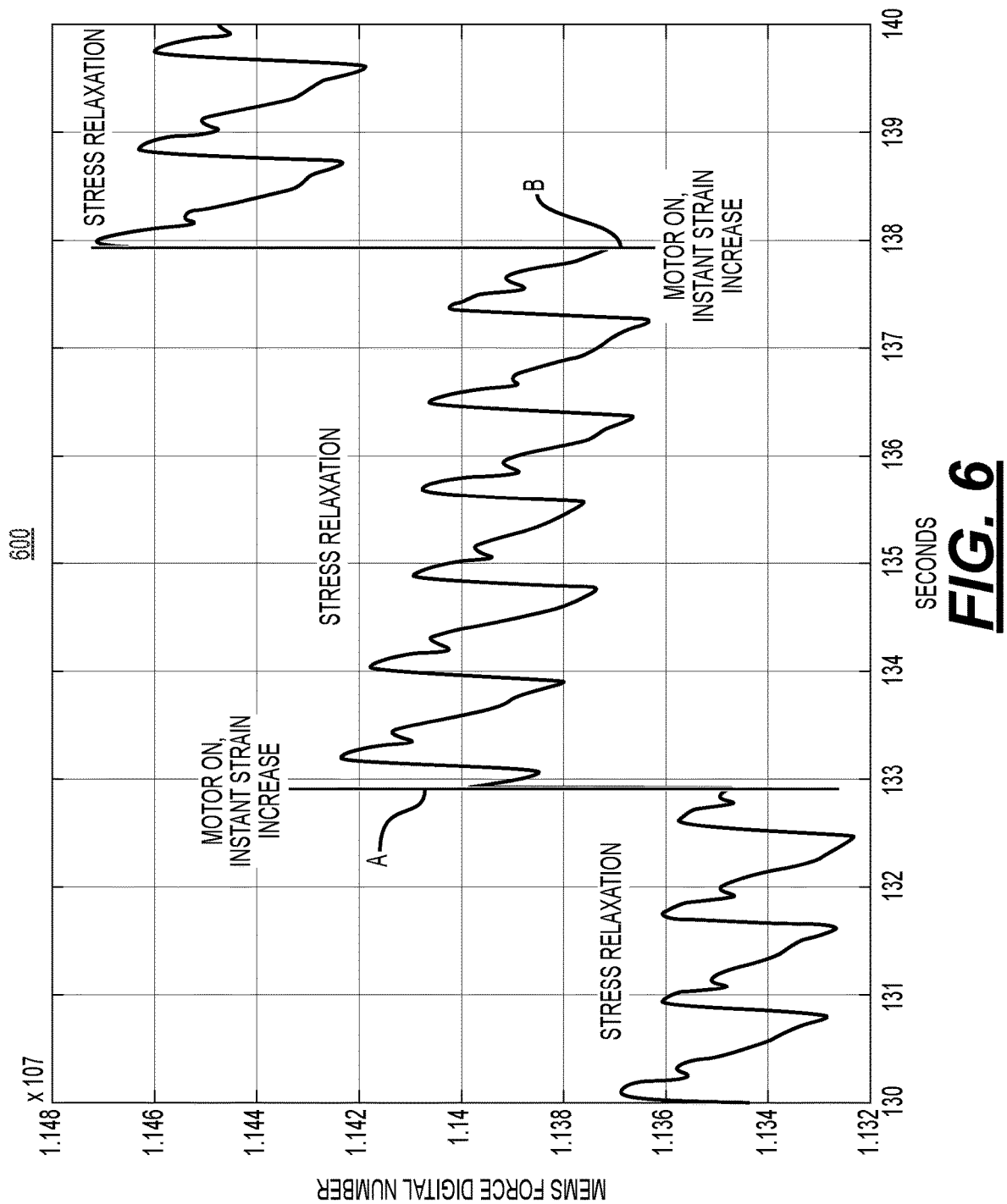
FIG. 6 is a chart that shows an example arterial blood pressure waveform superimposed on stress-relaxation kinetics created by visco-elastic response to instant strain increases created by ear-vise compression of ear tissue.

FIG. 6 is a chart 600 that shows an example arterial blood pressure waveform superimposed on stress-relaxation kinetics created by visco-elastic response to instant strain increases created by ear-vise compression of ear tissue. More particularly, FIG. 6 shows the stresses as measured when the ear-vise is placed on the ear and the motor is run briefly and then stopped for several seconds. Points A and B show the locations where the motor was turned on briefly. Note that the arterial blood pressure waveform is clearly superimposed upon the background stress relaxation kinetic.

Most oscillometric blood pressure measuring devices utilize a pneumatic cuff as the clamping mechanism for increasing and decreasing the compression pressure on the pulsatile tissue. A small pneumatic pump inflates the cuff to increase compression pressure, and an electrically operated air release valve controls the rate of deflation. These devices typically inflate at one speed; this is followed by a slower deflation of the cuff during which time the precise pulsatility measurements are acquired for assessment of systolic and diastolic pressure. Cuff deflation via the air release valve is continuous in nature; this continuity presents a smoothly continuously decreasing background pressure signal, upon which is superimposed the pulsatile waveform of the arterial blood pressure. The continuous (i.e., smooth) nature of the background deflating cuff pressure affords the precise measurement of pulsatile waveforms, upon which are based the estimates of diastolic and systolic blood pressure.

The device 100 performs compression and decompression via a digitally-controlled DC motor and gearbox. To change speeds of compression and decompression, the device 100 employs pulse width modulation (PWM). PWM cyclically turns the motor on for some percentage of the cycle (i.e., the duty cycle) and off for the rest of the cycle. Thus, the compression and decompression background forces are not continuously changed, instead they are changed discretely via the PWM. This creates the discontinuous background pressure measurement illustrated in FIG. 6. From a signal processing perspective, it is difficult to separate the discrete stress changes caused by the motor-initiation and subsequent visco-elastic response effects, from the desired pulsatile arterial blood pressure waveforms (again, see FIG. 6). Thus, the precision of the estimates of pulsatility required for determining systolic and diastolic pressure are hindered by these signal discontinuities. One could determine the exponential decay kinetics of the ear-vise assemblage, and subtract these from the measured waveform, in hope of obtaining a measure of the pulsatility free from visco-elastic discontinuities. However, every unique new device would have a different visco-elastic response kinetic, and the real-time signal processing using a model of multi-exponential decay kinetics would be computationally intensive (and would require higher sampling rates for more precision). The devices contemplated herein, such as the device 100 and the device 200, remove the visco-elastic response discontinuities.

Figure 7:
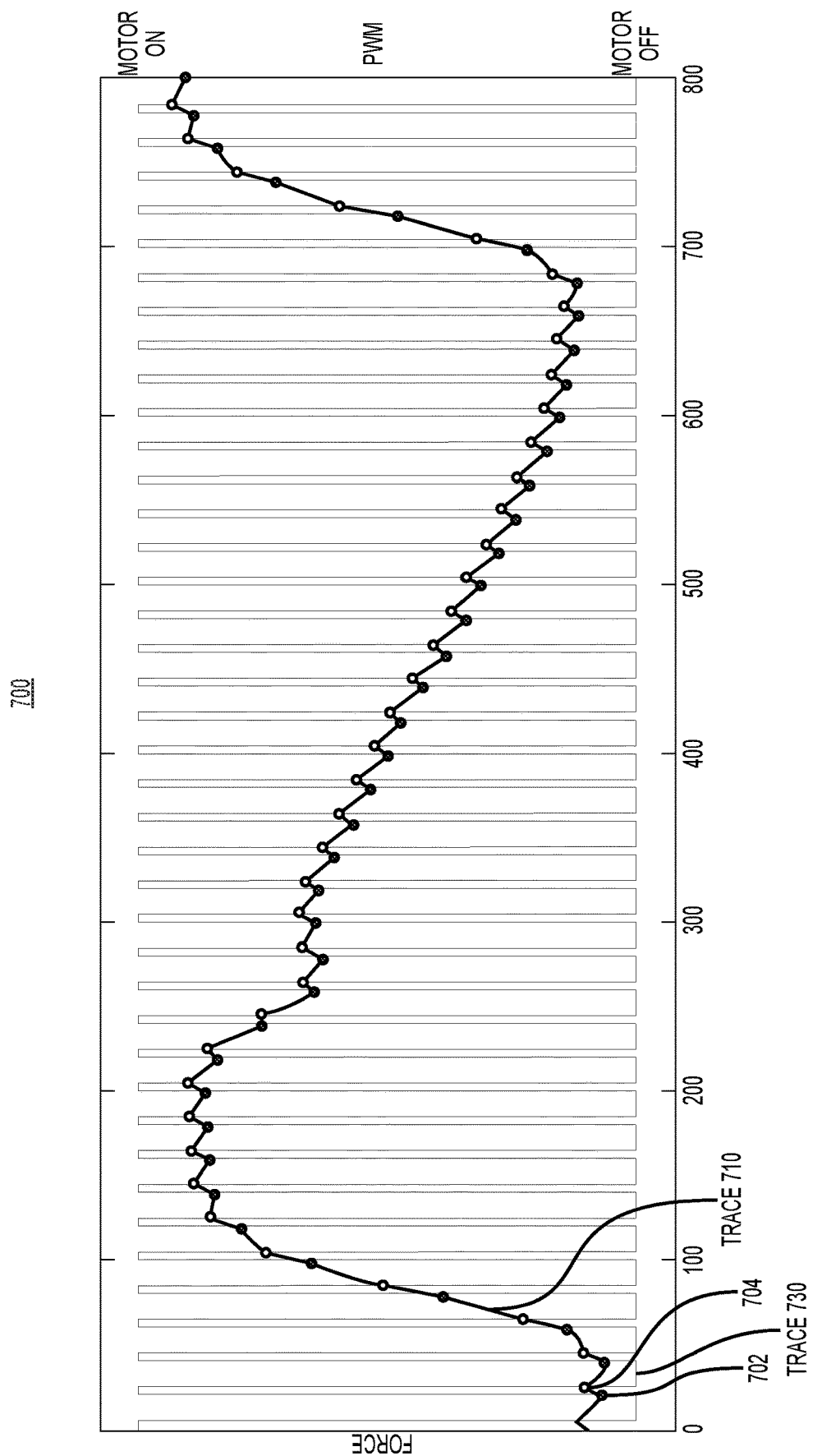
FIG. 7 is a chart that shows an example sketch of visco-elastic moto-phase sampling (VEMPS) methodology for sampling arterial blood pressure in phase with pulse width modulation (PWM)

FIG. 7 is a chart 700 that shows an example sketch of visco-elastic moto-phase sampling (VEMPS) methodology for sampling arterial blood pressure in phase with pulse width modulation (PWM). VEMPS is a term used to describe a technique that affords the precise measurement of pulsatile waveforms from any device employing a solid polymeric (visco-elastic) clip, such as the visco-elastic clip 182 or the visco-elastic clip 282. VEMPS removes the need for a pneumatic pressure pump (thus reducing size), and allows the pulsatile waveform estimates to proceed using any solid clip material/geometry and a computer-controlled DC motor/gearbox. Moreover, the technique requires no modeling of visco-elastic kinetics, minimizes real-time signal processing, is temperature independent, is solid material/geometry independent, and can work at all PWM motor speeds.

VEMPS works by phase-locking the sampling of the force sensor to a particular phase of the PWM signal. In an implementation, a device, such as the device 100, uses a 50 Hz PWM frequency to control the ear-vise motor speed; this corresponds to a 20 ms PWM cycle length (see e.g., FIG. 7). For VEMPS to work, the device must also use a 50 Hz analog to digital sampling frequency. This is convenient for the device because the onboard 24-bit sigma-delta analog to digital converter (ADC) has built-in digital low-pass filtering at 60 Hz and 50 Hz (designed around North American and UK home AC power grid frequencies, respectively). Moreover, the ADC can be controlled by an external clock, thus allowing for perfect synchronization of PWM motor-on events and ADC sampling. When the ADC sampling and ear-vise motor-on phases are synchronized, all the visco-elastic response effects are canceled, (because the visco-elastic response kinetics are constant, see FIG. 5). Thus, the ADC is repeatedly sampling at the same phase of PWM for every motor-on event (see FIG. 7). Thus, the current device uses VEMPS to negate the visco-elastic response discontinuities.

VEMPS allows for a sampling of a very precise stress/pressure waveform which can be used to accurately estimate real-time pulsatility, and thus real-time oscillometric diastolic and systolic blood pressures. In doing so, VEMPS allows the design to use any clip configuration or material, provided the material visco-elastic properties stay constant over the given stress/strain range. Essentially, VEMPS allows the design to use a solid clip as the force providing medium, and a digitally controlled gearbox motor for precise control. Moreover, VEMPS works during compression and decompression, allowing for two precise measurements of arterial pulsatility waveforms per calibration run. Additionally, VEMPS does not require the high sample-rate that would be needed for real-time accurate modeling of visco-elastic response behavior; this greatly reduces the number of floating point computations and thus greatly reduces battery consumption.

Thus, FIG. 7 shows a chart of VEMPS methodology for sampling arterial blood pressure in phase with PWM. The trace 710 is postulated force across the ear-vise showing visco-elastic response to PWM of the ear-vise motor (the trace 730). The light circles 702 show the start of ear-vice motor-on; the dark circles 704 show the end of motor-on and the time when ADC sample taken. By sampling the force curve at the end of the motor-on, the visco-elastic decay kinetics during motor-off do not contribute to the variability of the measured sample.

Figure 8:
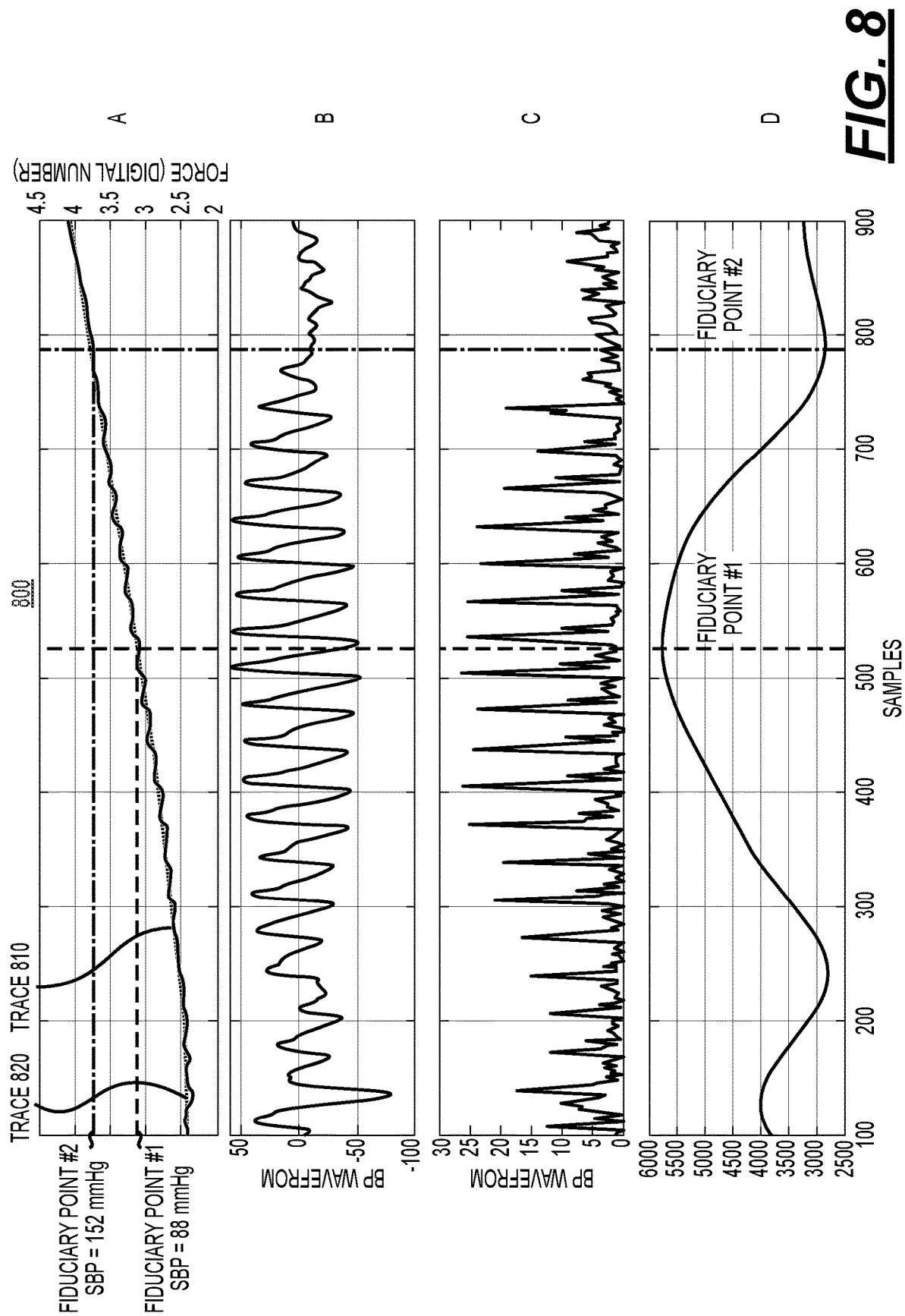
FIG. 8 is a chart of an example signal processing methodology that could be used to precisely locate the fiduciary points.

With respect to determining maximum pulsatility pressure and occlusion pressure, FIG. 8 is a chart 800 of an example signal processing methodology that could be used to precisely locate the fiduciary points.

The determination of diastolic blood pressure (DBP) and systolic blood pressure (SBP) requires two fiduciary points estimated from the force data acquired during steadily increasing compression of the ear tissue via the ear-vise. FIG. 8 shows the typical force data obtained during steadily increasing ear-vise compression. As applied compression force steadily increases, the pulsatility of the arterial blood pressure waveform reaches a point of maximum pulsatility (fiduciary point 1). At this point, the arterial blood pressure waveform has its maximum amplitude. As applied compression force increases further, the pulsatility of the arterial blood pressure waveform decreases until it reaches some minimum magnitude (fiduciary point 2). This point is referred to as the point of occlusion. There are several signal processing methodologies that could be used to precisely locate the fiduciary points. FIG. 8 is an illustration of one such methodology.

Real-time signal processing is used to locate the fiduciary points during a blood pressure determination compression run. FIG. 8 shows that the absolute value of the first-difference of the acquired force data (i.e., current sample force minus previous sample force) can be used, with further signal processing, to determine the two fiduciary points. FIG. 8 shows that a low-pass digital filter applied to the absolute of the first-difference data reveals the two fiduciary points: 1) the local maximum (fiduciary point 1), followed by 2) the next local minimum (fiduciary point 2). These two fiduciary points can then be used to estimate the ear-vise pressure of maximum pulsatility and occlusion. FIG. 8 shows the two fiduciary points projected onto the background force curve to obtain the measured force (and stress, i.e., measured force/ear-vise area). The background force curve is obtained via digital low-pass filtering of the force data sequence acquired during the compression run.

The measured force/stress at the two fiduciary points represent the device estimate of DBP and SBP for the individual subject during the time of measurement. For a large sample population, these device estimates are regressed against corresponding validated arm-cuff blood measurements to yield regression coefficients that can be used to determine standardized DBP and SBP measurements.

More particularly, in panel A of FIG. 8, the trace 810 is raw force data acquired during compression run, and the trace 820 is background force curve. Panel B shows the BP pulsatility curve during compression, showing maximum pulsatility and occlusion. Panel C shows the absolute value of the first differences of the raw force data. Panel D shows the results of low-pass digital filtering of the trace in panel C. The maximum is the fiduciary point #1 which is the point of maximum pulsatility. The minimum is the location of fiduciary point #2 which is the point of occlusion. These two points when projected on the background force curve yield the device estimate of diastolic and systolic blood pressure, respectively.

In some implementations, tissue compression does not occur at the ear, a compression drive mechanism is not at the ear, and a sensor is at the ear. In an implementation, the only thing mounted at the ear is the sensor/analog sampler/Bluetooth radio/micro-controller/flash RAM. Such an implementation has no mechanical workings mounted on the ear. Instead, the ear-mounted device is a passive ear clip designed to maintain a comfortable confining pressure at less than diastolic pressure (e.g., 30 mmHg). The clip contains the sensors and samples the sensor data for storage and/or radio/wire transmission.

This implementation works via a process of intermittent remote calibration. This process intermittently uses a compression drive and tissue/arterial compression at another body location, in conjunction with the continuous data obtained by the ear device. At intermittent times, the user might use a finger cuff BP device, or an upper arm inflationary cuff BP device to determine the "standard" BP. At this same time, the BP device transmits these latest BP measurements to the ear device (via radio or wire) such that the continuous pulsatility data obtained at the ear can be calibrated to match the "standard" BP data obtained at the other body location. Thus, the continuous ear data is intermittently and remotely calibrated. Moreover, if the inflatable finger cuff device is on the same side of the arterial tree as the ear clip, then intermittently also obtain simultaneous recordings at both sites; moreover, the ear and the fingertip are from the same branch of the arterial tree. The ear is more central representation of BP whereas the fingertip is much more distal representation of BP. The distal fingertip BP waveform is also more prone to a myriad of confounding augmentation waveforms from pressure reflections along the long arterial pathway. Additionally, the simultaneous recordings from the central and distal portions of the artery provide an opportunity to perform a transfer function analysis of the impedance properties of the arterial pathway. Moreover, one could also assess the travel times of the pulsatile waveform from the ear to fingertip, and this could provide other hitherto unknown pulse velocity data, which can be used for advanced assessment of cardiovascular wellness. It is noted that implementations described herein produce waveforms more akin to the aortic waveform. The central waveforms are the truest waveforms, without distortion from rebound waves from peripheral vessels in places like the fingers.

Advantages include, for example: increased accuracy at predicting clinical outcomes such as stroke, heart attack, and death; no need for modeling to get central arterial pressure; and it is more straightforward to calculate stroke volume and peripheral vascular resistance from this pure signal, which in turn permits precision medicine treatment with different drug classes for heart failure and hypertension, and from hundreds of miles away.

In an embodiment of intermittent remote calibration, a smart phone protective case has a molded latex finger port, or a flip-up finger port, and upon fingertip insertion, an algorithm controls a small gearbox motor that adjusts a confining pressure applied between the nail bed and the finger tissue to determine systolic and diastolic BP, all the while in radio connection with the passive ear cuff and the smart phone. At this time, the ear cuff data gets remotely calibrated, and the transfer function between the ear and fingertip is determined and stored for future analysis. Via radio link (e.g., BluetoothLE), the ear clip and the smart phone can then inform the user when another remote calibration is necessary, or the user can perform the remote calibration at their discretion.

Another embodiment uses a device similar in size to a USB memory stick. The gearbox motor is mounted inside the device and the conventional USB interface becomes a high speed serial interface for data download, and a charging port for the device and for the ear clip. This device would not require a smart phone.

With respect to the intermittent remote calibration devices described above, by removing the motor/gearbox and ear-vise from the ear site itself, the entire device at the ear becomes an order of magnitude smaller in size and mass. This affords a much more stable platform. Moreover, the power consumption at the ear is also greatly reduced allowing for longer wearing times between battery recharges. Furthermore, by intermittently having sensors at both ends of the arterial vascular tree (i.e., the ear and the fingertip), this allows for real-time intermittent determination of measured vascular impedance (as opposed to theoretical impedance offered by others), something unique to the field. In addition, this multi-sensor platform (albeit intermittent in the described embodiment) is a first step into the multi-sensor domain. The appeal of the ultra-small and ultra-light ear sensor, used intermittently in conjunction with a tiny memory-stick sized USB device is not to be overlooked. This industry-wide move into multi-sensor wearables is going to eventually happen; the intermittent remote calibration arrangement described above is one feasible step in this direction.

Figure 9:
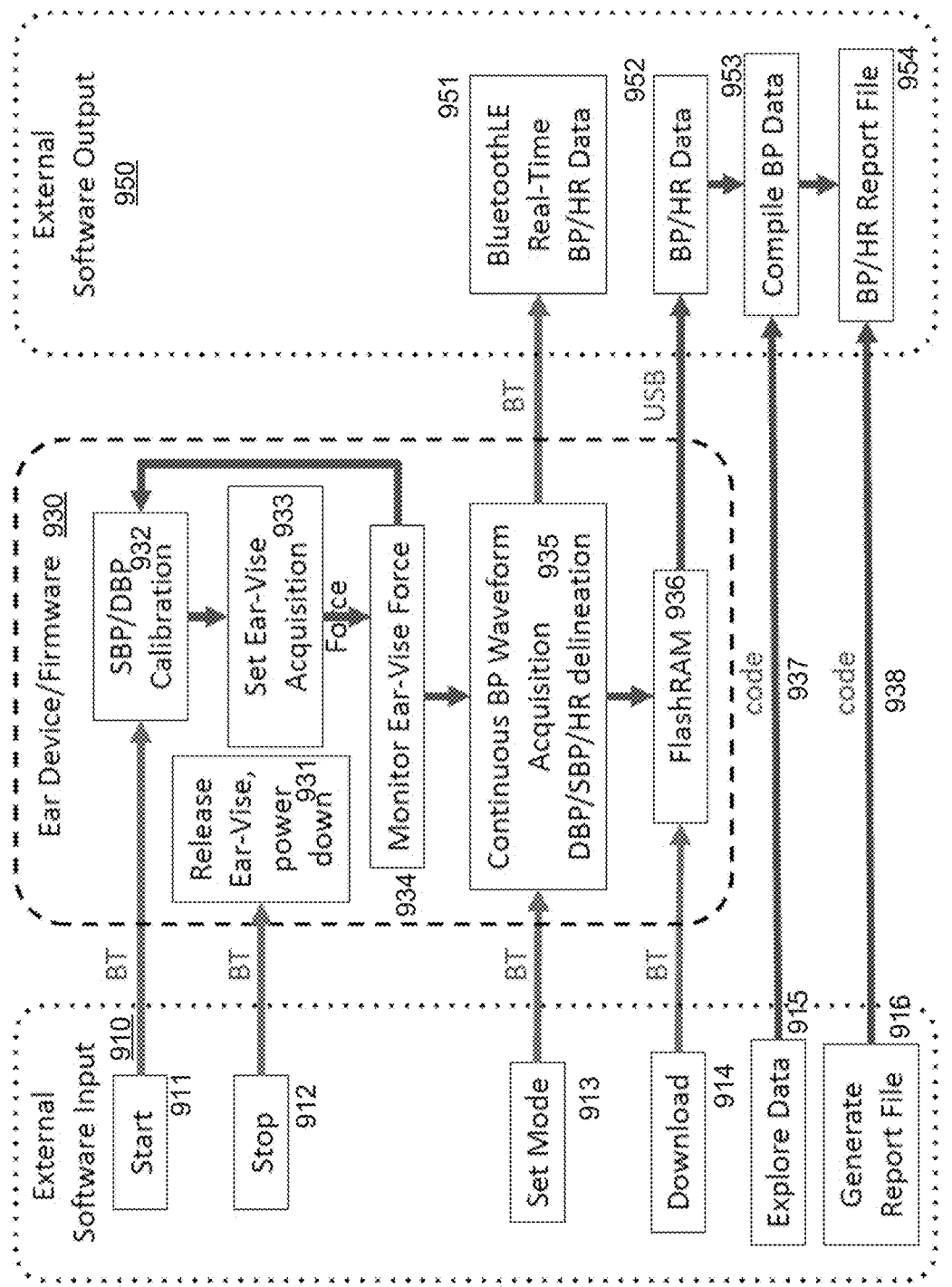
FIG. 9 is a diagram of an implementation of a system for blood pressure measurement with a wearable cardiovascular monitoring device.

FIG. 9 is a diagram of an implementation of a system 900 for blood pressure measurement with a wearable cardiovascular monitoring device. The system comprises external software input 910, an ear device (firmware) 930, and external software output 950.

The external software input 910 may comprise inputs to the ear device 930 such as start 911, stop 912, set mode 913, download 914, explore data 915, and generate report file 916, for example, though these are not intended to be limiting. The inputs to the ear device 930 are not limited to those listed, and may comprise more or fewer inputs depending on the implementation. The inputs may be provided to the ear device (firmware) 930 using BluetoothLE (Bluetooth Low Energy, also referred to herein at BT).

The ear device 930 may comprise a release ear-vise, power down module 931, a systolic blood pressure (SBP)/diastolic blood pressure (DBP) calibration module 932, a set ear-vise acquisition module 933, a monitor ear-vise force module 934, a continuous blood pressure acquisition with DBP/SBP/heart rate (HR) delineation module 935, and flash memory such as flash RAM 936, for example, though these are not intended to be limiting. The ear device 903 may comprise more or fewer modules and/or components than those listed, depending on the implementation.

The SBP/DBP calibration module 932 may be actuated or started pursuant to receiving the start 911 input. The release ear-vise, power down module 931 may be actuated or started pursuant to receiving the stop 912 input.

After the SBP/DBP calibration module 932 performs calibration of the ear device 930, the set ear-vise acquisition module 933 is actuated or started which then actuates or starts the monitor ear-vise force module 934. The continuous BP acquisition with DBP/SBP/HR delineation module 935 is then begun, followed by storage of the acquired data in the flash RAM 936.

The external software output 950 may comprise BT real-time BP/HR data 951 received from the continuous BP acquisition with DBP/SBP/HR delineation module 935. The BluetoothLE real-time BP/HR data 951 may be obtained or otherwise received or retrieved pursuant to the set mode 913 input of the external software input 910, which may provide instructions to the ear device 930, and thus the a continuous BP acquisition with DBP/SBP/HR delineation module 935, by BT in some implementations.

The external software output 950 may also receive BP/HR data 952 from storage of the ear device 930, such as from the flash RAM 936 via USB. The BP/HR data 952 may be obtained or otherwise received or retrieved pursuant to the download 914 input of the external software input 910, which may provide instructions to the ear device 930, and thus the flash RAM 936, by BT in some implementations.

The BP data from the BP/HR data 952 may be compiled into compiled BP data 953 (e.g., pursuant to the explore data 915 input of the external software input 910 using code 937 to compile the BP data).

A BP/HR report file 954 may be generated (e.g., pursuant to the generate report file 916 input of the external software input 910 using code 938 to generate the BP/HR report file 954) and stored and/or otherwise outputted.

Figure 10:
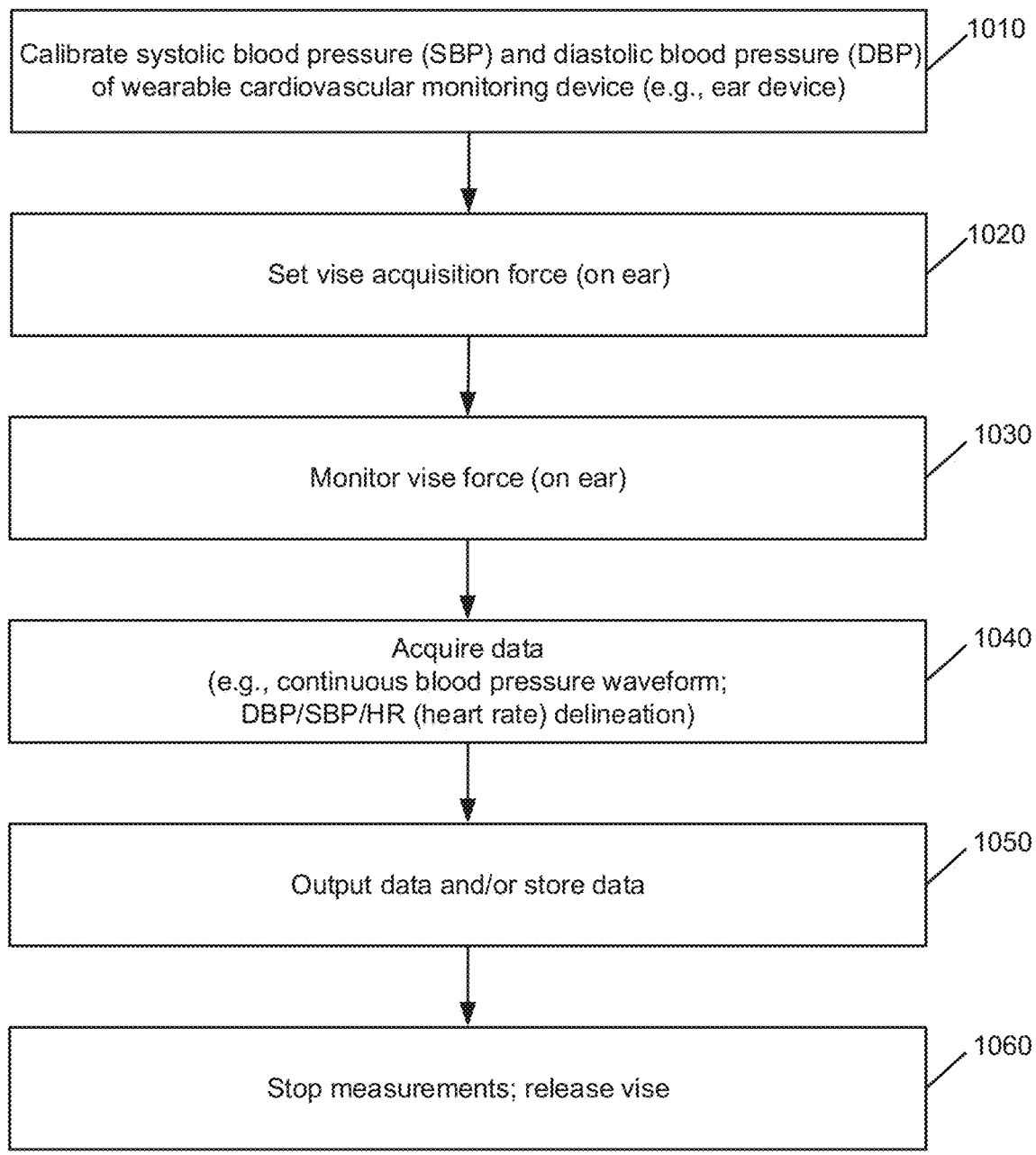
FIG. 10 is an operational flow of another implementation of a method for blood pressure measurement with a wearable cardiovascular monitoring device.

FIG. 10 is an operational flow of another implementation of a method 1000 for blood pressure measurement with a wearable cardiovascular monitoring device, such as the wearable cardiovascular monitoring device 100 or the ear device 930, for example.

At 1010, the device (e.g., the wearable cardiovascular monitoring device 100 or the ear device 930) is calibrated. For example, the SBP and the DBP is calibrated by firmware of the device, pursuant to a start command being received (e.g., the start 911 input of an external software input 910).

At 1020, the vise acquisition force (e.g., for the ear) is set. This may be set to a predetermined amount or set to an amount pursuant to a predetermined technique or algorithm.

At 1030, force is applied (e.g., to the ear) and monitored to ensure that the force is maintained at the proper amount from 1020.

At 1040, data is acquired by the device. Depending on the implementation, data may include a continuous blood pressure waveform, and/or DBP, SBP, HR delineation.

At 1050, the data that was acquired at 1040 may be stored (e.g., in memory or storage of the device, such as flash RAM or other local or external storage). Alternatively or additionally, the data may be outputted or displayed to one or more other devices, for example.

At 1060, the measurements stop (e.g., pursuant to a stop 912 input being received), and the vise is released.

More generally, in this specification, including the claims, the term "processing circuit" is intended to broadly encompass any type of device or combination of devices capable of performing the functions described herein, including (without limitation) other types of microprocessing circuits, microcontrollers, other integrated circuits, other types of circuits or combinations of circuits, logic gates or gate arrays, or programmable devices of any sort, for example, either alone or in combination with other such devices located at the same location or remotely from each other. Additional types of processing circuit(s) will be apparent to those ordinarily skilled in the art upon review of this specification, and substitution of any such other types of processing circuit(s) is considered not to depart from the scope of the present invention as defined by the claims appended hereto. In various embodiments, the processing circuit can be implemented as a single-chip, multiple chips and/or other electrical components including one or more integrated circuits and printed circuit boards.

Computer code comprising instructions for the processing circuit(s) to carry out the various embodiments, aspects, features, etc. of the present disclosure may reside in the memory. In various embodiments, the processing circuit can be implemented as a single-chip, multiple chips and/or other electrical components including one or more integrated circuits and printed circuit boards. The processing circuit together with a suitable operating system may operate to execute instructions in the form of computer code and produce and use data. By way of example and not by way of limitation, the operating system may be Windows-based, Mac-based, or Unix or Linux-based, among other suitable operating systems. Operating systems are generally well known and will not be described in further detail here.

Memory may include various tangible, non-transitory computer-readable media including Read-Only Memory (ROM) and/or Random-Access Memory (RAM). As is well known in the art, ROM acts to transfer data and instructions unidirectionally to the processing circuit, and RAM is used typically to transfer data and instructions in a bi-directional manner. In the various embodiments disclosed herein, RAM includes computer program instructions that when executed by the processing circuit cause the processing circuit to execute the program instructions described in greater detail below. More generally, the term "memory" as used herein encompasses one or more storage mediums and generally provides a place to store computer code (e.g., software and/or firmware) and data that are used by the control system. It may comprise, for example, electronic, optical, magnetic, or any other storage or transmission device capable of providing the processing circuit with program instructions. Memory may further include a floppy disk, CD-ROM, DVD, magnetic disk, memory chip, ASIC, FPGA, EEPROM, EPROM, flash memory, optical media, or any other suitable memory from which processing circuit can read instructions in computer programming languages.

FIG. 11 shows an exemplary computing environment in which example embodiments and aspects may be implemented. The computing device environment is only one example of a suitable computing environment and is not intended to suggest any limitation as to the scope of use or functionality.

Numerous other general purpose or special purpose computing devices environments or configurations may be used. Examples of well-known computing devices, environments, and/or configurations that may be suitable for use include, but are not limited to, personal computers, server computers, handheld or laptop devices, multiprocessor systems, microprocessor-based systems, network personal computers (PCs), minicomputers, mainframe computers, embedded systems, distributed computing environments that include any of the above systems or devices, and the like.

Computer-executable instructions, such as program modules, being executed by a computer may be used. Generally, program modules include routines, programs, objects, components, data structures, etc. that perform particular tasks or implement particular abstract data types. Distributed computing environments may be used where tasks are performed by remote processing devices that are linked through a communications network or other data transmission medium. In a distributed computing environment, program modules and other data may be located in both local and remote computer storage media including memory storage devices.

With reference to FIG. 11, an exemplary system for implementing aspects described herein includes a computing device, such as computing device 1100. In its most basic configuration, computing device 1100 typically includes at least one processing unit 1102 and memory 1104. Depending on the exact configuration and type of computing device, memory 1104 may be volatile (such as random access memory (RAM)), non-volatile (such as read-only memory (ROM), flash memory, etc.), or some combination of the two. This most basic configuration is illustrated in FIG. 11 by dashed line 1106.

Computing device 1100 may have additional features/functionality. For example, computing device 1100 may include additional storage (removable and/or non-removable) including, but not limited to, magnetic or optical disks or tape. Such additional storage is illustrated in FIG. 11 by removable storage 1108 and non-removable storage 1110.

Computing device 1100 typically includes a variety of computer readable media. Computer readable media can be any available media that can be accessed by the device 1100 and includes both volatile and non-volatile media, removable and non-removable media.

Computer storage media include volatile and non-volatile, and removable and non-removable media implemented in any method or technology for storage of information such as computer readable instructions, data structures, program modules or other data. Memory 1104, removable storage 1108, and non-removable storage 1110 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 1100. Any such computer storage media may be part of computing device 1100.

Computing device 1100 may contain communication connection(s) 1112 that allow the device to communicate with other devices. Computing device 1100 may also have input device(s) 1114 such as a keyboard, mouse, pen, voice input device, touch input device, etc. Output device(s) 1116 such as a display, speakers, printer, etc. may also be included. All these devices are well known in the art and need not be discussed at length here.

It should be understood that the various techniques described herein may be implemented in connection with hardware components or software components or, where appropriate, with a combination of both. Illustrative types of hardware components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc. The methods and apparatus of the presently disclosed subject matter, or certain aspects or portions thereof, may take the form of program code (i.e., instructions) embodied in tangible media, such as floppy diskettes, CD-ROMs, hard drives, or any other machine-readable storage medium where, when the program code is loaded into and executed by a machine, such as a computer, the machine becomes an apparatus for practicing the presently disclosed subject matter.

In an implementation, a wearable cardiovascular monitoring device comprises: a first portion configured to be worn on a first side of an ear of a human with a first vise face for contacting the first side of the ear; a second portion configured to be worn on a second side of the ear with a second vise face for contacting the second side of the ear, wherein the second portion comprises a force sensor configured for a blood pressure measurement; and a third portion configured to be worn over the ear and attached to the first portion and the second portion.

Implementations may include some or all of the following features. The first portion comprises an electronics portion configured to perform visco-elastic moto-phase sampling. The first portion comprises a motor, a gearbox, and a gear, wherein the gear is in contact with the first vise face. The visco-elastic moto-phase sampling of the first portion samples the motor and provides the samples via a sensor bus to an analog to digital converter (ADC). The ADC is comprised within the second portion. The third portion comprises a visco-elastic clip. The first side of the ear is behind the ear, and the second side of the ear is in front of the ear. The first vise face and the second vise face are comprised within an ear-vise, wherein the ear-vise is an oscillometric device such that a confining pressure is applied to tissue of the ear and the contained pulsating arteries of the ear inflate and deflate under confining pressure causing a plurality of pulsatile changes in a measured parameter of the tissue of the ear. The confining pressure is applied perpendicular to a planar surface of the ear via the ear-vise.

In an implementation, a cardiovascular monitoring device comprises: an ear-vise comprising a first vise face and a second vise face configured to apply pressure to an ear; and a sensor for measuring blood pressure using the pressure applied to the ear.

Implementations may include some or all of the following features. The first vise face contacts one side of the ear, and the second vise face contacts another side of the ear. The ear-vise is configured to apply pressure to tissue of the ear and pulsating arteries of the ear inflate and deflate under confining pressure causing a plurality of pulsatile changes in a measured parameter of the tissue of the ear. The first vise face is disposed such that a compressive force causes a micron scale displacement that is converted to a voltage proportional to force. The cardiovascular monitoring device further comprises a gearbox and motor that generate the compressive force, wherein a plurality of pulsatile blood pressure changes further generate the compressive force. The micron scale displacement is measured across compressed ear tissue or measured on one side of the ear behind the first vise face or behind the second vise face.

In an implementation, a method for blood pressure measurement of a person comprises: setting a vise acquisition force of a wearable cardiovascular monitoring device on an ear of the person; monitoring a vise force of the wearable cardiovascular monitoring device on the ear; acquiring data from the wearable cardiovascular monitoring device on the ear; and outputting the acquired data.

Implementations may include some or all of the following features. Acquiring the data comprises acquiring a continuous blood pressure waveform. Acquiring the data further comprises performing diastolic blood pressure, systolic blood pressure, and heart rate delineation. The method further comprises compiling the acquired data and generating a report file. The method further comprises calibrating systolic blood pressure and diastolic blood pressure of the wearable cardiovascular monitoring device.

Although exemplary implementations may refer to utilizing aspects of the presently disclosed subject matter in the context of one or more stand-alone computer systems, the subject matter is not so limited, but rather may be implemented in connection with any computing environment, such as a network or distributed computing environment. Still further, aspects of the presently disclosed subject matter may be implemented in or across a plurality of processing chips or devices, and storage may similarly be effected across a plurality of devices. Such devices might include personal computers, network servers, and handheld devices, for example.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. An earworn cardiovascular monitoring device comprising:
   a first portion configured to be worn on a first side of an ear of a human comprising:
      a first housing with a gearbox and a motor within the housing; and
      a first vise face connected to the gearbox and the motor, wherein the gearbox and the motor are configured to apply pressure to the ear;
   a second portion configured to be worn on a second side of the ear of the human comprising:
      a second vise face; and
      a passive resistive sensor for measuring blood pressure by sensing the pressure applied to the ear by the first vise face and the second vise face; and
   a micro-controller, a memory that stores data acquired by the earworn cardiovascular monitoring device; and a low energy wireless communication device to communicate the data to an external device.

2. The earworn cardiovascular monitoring device of claim 1, wherein the first vise face is configured to contact one side of the ear, and the second vise face is configured to contact another side of the ear.

3. The earworn cardiovascular monitoring device of claim 1, wherein the first vise face and second vise face are configured to apply a confining pressure to tissue of the ear such that pulsating arteries of the ear inflate and deflate under the confining pressure causing a plurality of pulsatile changes in a measured parameter of the tissue of the ear.

4. The earworn cardiovascular monitoring device of claim 1, wherein the first vise face is disposed such that a compressive force causes a micron scale displacement between 50-100 microns that is converted to a voltage proportional to force.

5. The earworn cardiovascular monitoring device of claim 4, wherein the gearbox and the motor generate the compressive force.

6. The earworn cardiovascular monitoring device of claim 4, wherein the micron scale displacement is measured across compressed ear tissue or measured on one side of the ear behind the first vise face or behind the second vise face.

7. The earworn cardiovascular monitoring device of claim 1, wherein further comprising an external software input adapted to receive commands to control the device.

8. The earworn cardiovascular monitoring device of claim 7, wherein the external software input receives the commands using the low energy wireless communication device.

9. The earworn cardiovascular monitoring device of claim 1, further comprising a systolic blood pressure (SBP)/diastolic blood pressure (DBP) calibration module that calibrates the device.

10. The earworn cardiovascular monitoring device of claim 1, further comprising a continuous blood pressure acquisition with a diastolic blood pressure (DBP)/systolic blood pressure (SBP)/heart rate (HR) delineation module that acquires the data from the force sensor and stores the data in the memory.

11. The earworn cardiovascular monitoring device of claim 1, further comprising an external software output that receives the data from the memory and communicates the data over the low energy wireless communication device to the external device.

* * * * *